US006811565B2

United States Patent
Denton et al.

(10) Patent No.: US 6,811,565 B2
(45) Date of Patent: Nov. 2, 2004

(54) SYSTEM AND METHOD FOR LIGHT ACTIVATION OF HEALING MECHANISMS

(75) Inventors: David G. Denton, Issaquah, WA (US); Serene Murray-Denton, Issaquah, WA (US); Larry Azure, La Conner, WA (US)

(73) Assignee: Healing Machines, Inc., La Conner, WA (US)

( * ) Notice: Subject to any disclaimer, the term of this patent is extended or adjusted under 35 U.S.C. 154(b) by 0 days.

(21) Appl. No.: 09/991,129

(22) Filed: Nov. 14, 2001

(65) Prior Publication Data

US 2003/0093135 A1 May 15, 2003

(51) Int. Cl.⁷ .................................................. A61N 5/06
(52) U.S. Cl. ........................... 607/91; 128/898; 607/88
(58) Field of Search ...................................... 607/88–95

(56) References Cited

U.S. PATENT DOCUMENTS

| 4,505,545 | A | * | 3/1985 | Salia-Munoz | 607/90 |
| 4,901,724 | A | * | 2/1990 | Mori | 607/95 |
| 5,519,534 | A | | 5/1996 | Smith et al. | 359/599 |
| 5,643,333 | A | * | 7/1997 | Yun | 607/88 |
| 5,824,023 | A | | 10/1998 | Anderson | 607/88 |
| 5,843,143 | A | * | 12/1998 | Whitehurst | 607/88 |
| 6,261,310 | B1 | | 7/2001 | Neuberger et al. | 607/89 |
| 6,402,681 | B1 | * | 6/2002 | McDonough et al. | 607/88 |
| 6,443,978 | B1 | * | 9/2002 | Zharov | 607/91 |
| 6,641,578 | B2 | * | 11/2003 | Mukai | 606/9 |
| 6,706,035 | B2 | * | 3/2004 | Cense et al. | 606/9 |
| 2002/0120312 | A1 | * | 8/2002 | Ignatius et al. | 607/90 |
| 2002/0173780 | A1 | * | 11/2002 | Altshuler et al. | 607/88 |

FOREIGN PATENT DOCUMENTS

| DE | 92 09 379.5 | 12/1992 |
| EP | 0 416 150 A1 | 3/1991 |
| EP | 1 118 311 A2 | 7/2001 |
| EP | 1 147 786 A2 | 10/2001 |
| GB | 2 272 278 A | 5/1994 |
| WO | WO 90/00420 | 1/1990 |

* cited by examiner

Primary Examiner—Roy D. Gibson
Assistant Examiner—Henry M Johnson, III
(74) Attorney, Agent, or Firm—Stoel Rives LLP

(57) ABSTRACT

A system and method for the light activation of healing processes uses a light source that is directed onto the body of a subject. The light source may generate monochromatic light and/or coherent light. The subject is positioned within a chamber having interior reflective surfaces that permit the reflection of photonic energy emitted from the body of the subject to be reflected back to the subject. The light source activates the photonic emission process. In an alternative embodiment, reflective surfaces may be brought into proximity or into direct contact with the subject and the light source directed onto the subject. The light source may be held in fixed position with respect to the subject or moved so as to be directed to an area of the subject. The light source may have a fixed intensity or varying intensity, such as by pulsing or modulating light source.

14 Claims, 8 Drawing Sheets

SYSTEM AND METHOD FOR LIGHT ACTIVATION OF HEALING MECHANISMS

BACKGROUND OF THE INVENTION

1. Field of the Invention

The present invention is related generally to techniques to assist the body in self-healing and, more particularly, to a system and method for activation of healing mechanisms using light.

2. Description of the Related Art

The human body emits a form of light energy that may be described as an auric field. This auric field may be visualized using known technologies, such as Kirlian photography and other modalities. Scientists have determined that the light energy emitted from the body is the result of photons circulating among molecules and being passed from one atom to another. Scientists hypothesize that molecules, including deoxyribonucleic acid (DNA) may function as selective resonators for photon information and energy. For example, it is known that in the presence of structural subluxations of the cranium, spine, extremities, muscular spasms and ligamentous inflammation, there is an alteration and intensification of light emissions at the point of dysfunction. As noted above, Kirlian photography may be used to indicate the presence of such dysfunctions.

Despite the ability to measure such variations in photonic emission from the body, there is presently no suitable mechanism for utilizing this information to activate healing processes within the body. Therefore, it can be appreciated that there is a significant need for a system and method for activation of healing processes within the body using such emissions. The present invention provides this and other advantages as will be apparent from the following detailed description and accompanying figures.

BRIEF SUMMARY OF THE INVENTION

The present invention is embodied in a system which, in an exemplary embodiment, comprises a chamber sized to hold an individual subject with the chamber having an interior portion defined by chamber walls. A reflective surface covers at least a portion of the interior portion of the chamber to reflect energy. A light source is used to deliver light to the subject within the chamber. In an exemplary embodiment, the light source may be a monochromatic light source and, in one embodiment, may be a coherent light source. In one embodiment, the reflective surface is a mirrored surface. The reflective surface may be designed to reflect electromagnetic energy from the surface of the subject within the interior portion of the chamber.

Alternatively, the system may comprise a reflective surface positioned proximate the surface of a subject at a predetermined location on the subject surface to reflect energy. The light source is used to deliver light to the subject. In one embodiment, the system may include a garment sized to be worn by the subject wherein the reflective surface is mounted on an interior portion of the garment and brought into proximity with the subject surface when the garment is worn by the subject. The reflective surface may comprise a plurality of mirrors positioned at predetermined locations along the surface of the subject.

The light may be selected to have wavelengths in the visible portion of the spectrum. The light source may be located in a fixed position with respect to the subject such that the light is directed to a substantially fixed position on the surface of the subject. Alternatively, the light source may be moveable with respect to the subject and may be repositioned while active to thereby direct light to an area on the surface of the subject. The light may have a substantially constant light intensity or, in an alternative embodiment, may emit a variable light intensity on the surface of the subject. The light source may be implemented with monochromatic light or, in an exemplary embodiment, with a coherent light source. In one embodiment, the coherent light source is a laser. In an exemplary embodiment, the laser is a class 3 laser.

The light source may be mounted within a container comprising a top portion and side portions and a visually transparent bottom portion to permit the passage of the light. The reflective surface may be affixed to the container proximate the bottom portion. The reflective surface may have an aperture to permit passage of light to the subject. In one embodiment, the bottom portion may comprise a clear glass surface. Alternatively, the bottom portion may be manufactured from a filter material to permit passage of selected wavelengths of light generated by the light source.

In yet another alternative, the bottom portion may comprise a glass surface shaped to form a lens to thereby focus the light in a predetermined manner.

The container may further comprise an opaque member surrounding the visually transparent bottom portion to prevent the application of light outside the opaque member when the bottom portion of the container is placed in proximity with the subject. In one embodiment, the opaque member may be black. The opaque member may also be manufactured from a pliable material. If the container housing the light source is cylindrical in shape, the opaque member may be substantially circular.

DETAILED DESCRIPTION OF THE INVENTION

In their book "The Living Energy Universe," Drs. Schwartz and Russek quote another scientist who states that human DNA may function as a receiver for a class of photons called biophotons. DNA and other molecules may function as selective resonators for photonic information. The reflection of light emitted from the body reflects back a memory of what should or could be a normal physiologic function and thereby assists in biologic retrieval and reprogramming of systems and tissues to aid in their return to correct functionality. The present invention is directed to a technique to activate the body's self-healing mechanisms through the use of monochromatic and/or coherent light and reflective surfaces to reflect the body's own electromagnetic emissions.

For example, a reflection of increased or intensified light emissions at the point of dysfunction, such as are known to occur in the locale of muscular spasms and ligamentous inflammation helps redirect the body's energy to correct the dysfunction and thus assists in the self-healing process.

Figure 1:
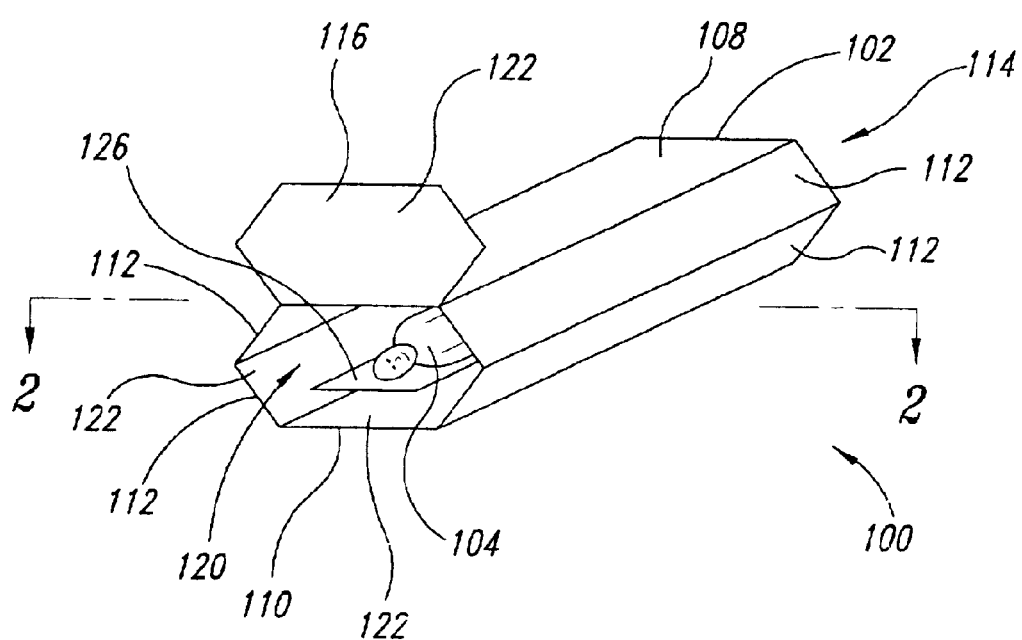
FIG. 1 is a perspective view of a chamber in which a patient is placed for treatment.

The invention may be embodied in a system 100, illustrated in FIG. 1, and includes a chamber 102 which is sufficiently large to accommodate a subject 104. In the embodiment illustrated in FIG. 1, the chamber 100 is hexagonal in cross-section and comprises a top panel 108, a bottom panel 110, and side panels 112. The chamber 102 also includes an end panel 114 and a door panel 116 through which the subject 104 gains access to an interior portion 120 of the chamber 102. In the embodiment illustrated in FIG. 1, the door panel 116 is attached to the top panel 108 by hinges or other conventional means. Alternatively, the door panel 116 may be attached to the bottom 110. In yet another alternative embodiment, access to the interior portion 120 of the chamber 102 may be provided by coupling the top panel 108 to a side panel 112 with hinges (not shown) or other conventional means. Those skilled in the art will recognize that a variety of such combinations may be provided to allow the subject 104 access to the interior portion 120 of the chamber 102.

The inside portions of the various panels facing the interior portion 120 of the chamber 102 are lined with a reflective surface 122. In one embodiment, the reflective surface 122 may comprise mirrors mounted on the inside portions of the top panel 108, bottom panel 110, side panels 112, end panel 114 and door panel 116. Alternatively, the reflective surface 122 may be mylar, polished metal, or mirrored surface manufactured on, by way of example, plastic.

Figure 2:
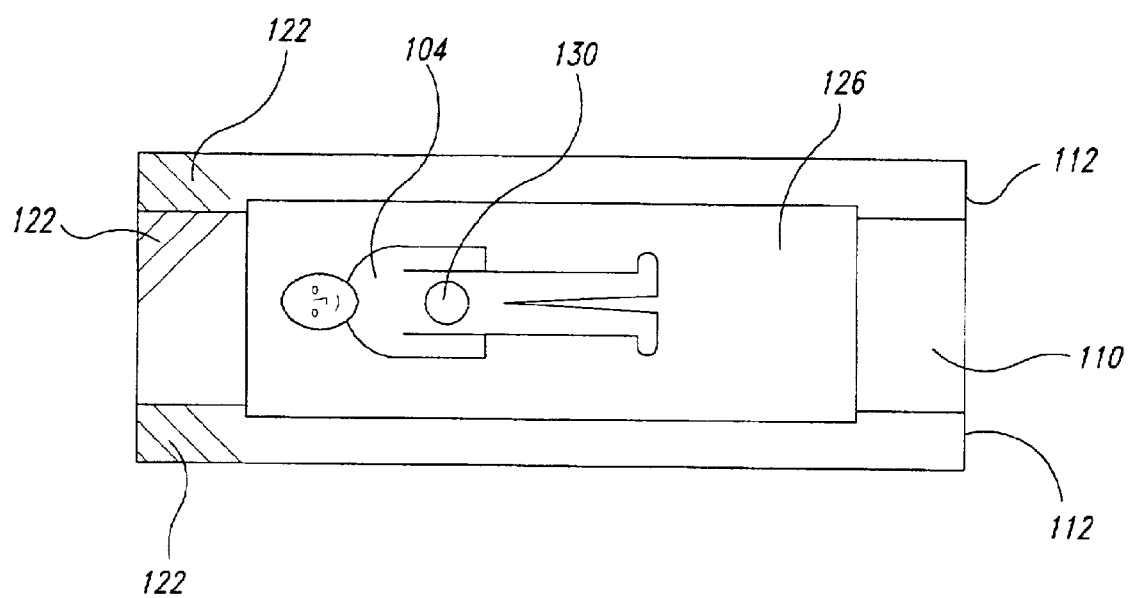
FIG. 2 is a top plan view of the chamber of FIG. 1 taken along the lines 2—2.

The chamber 102 illustrated in FIG. 1 is also shown in a cross-section along the line 2—2 in FIG. 2. As can best be seen in FIG. 2, the subject 104 is placed on a support member 126, such as a table. The support member 126 may be mounted on rollers (not shown) such that the support member 126 may easily slide out of the interior portion 120 (see FIG. 1) via the door panel 116 to allow the subject 104 to enter and exit the chamber 102. The support member 126 allows the subject 104 to be placed in a prone position or, as illustrated in FIGS. 1 and 2, in a supine position within the interior portion 120 of the chamber 102.

Also illustrated in FIG. 2 is a container or housing 130 for a light source 150. As illustrated in FIG. 2, the housing 130 is positioned proximate the trunk of the subject 104 and activated to trigger a healing response in the subject. Details of the housing 130 and light source 150 will be provided below.

Figure 3:
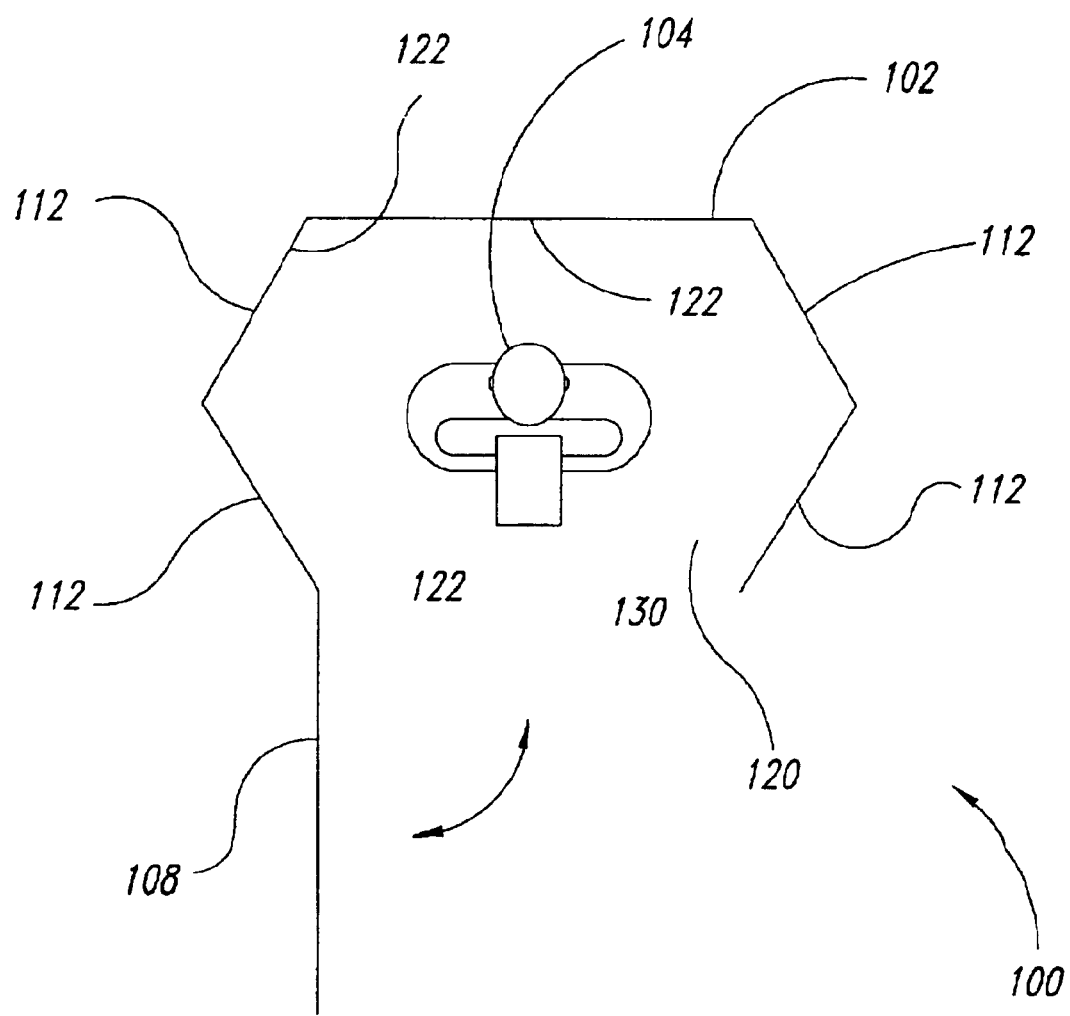
FIG. 3 is a top plan view of an alternative embodiment of the chamber of the present invention.

The chamber 102 illustrated in FIGS. 1 and 2 is oriented in a substantially horizontal configuration to allow the subject 104 to be placed in a prone or supine position within the interior portion 120 of the chamber. However, the system 100 may be implemented with chambers having different orientations and different configurations. For example, FIG. 3 is a top plan view of the chamber 102 in a substantially vertical orientation to allow the subject 104 to enter the interior portion 120 in a standing position. In the embodiment illustrated in FIG. 3, the top panel 108 is hinged and functions as a door to allow the subject 104 to enter and exit the interior portion 120 of the chamber 102. The reflective surfaces 122 function in a manner previously described above to reflect energy emitted from the subject 104 back to the subject.

Figure 4:
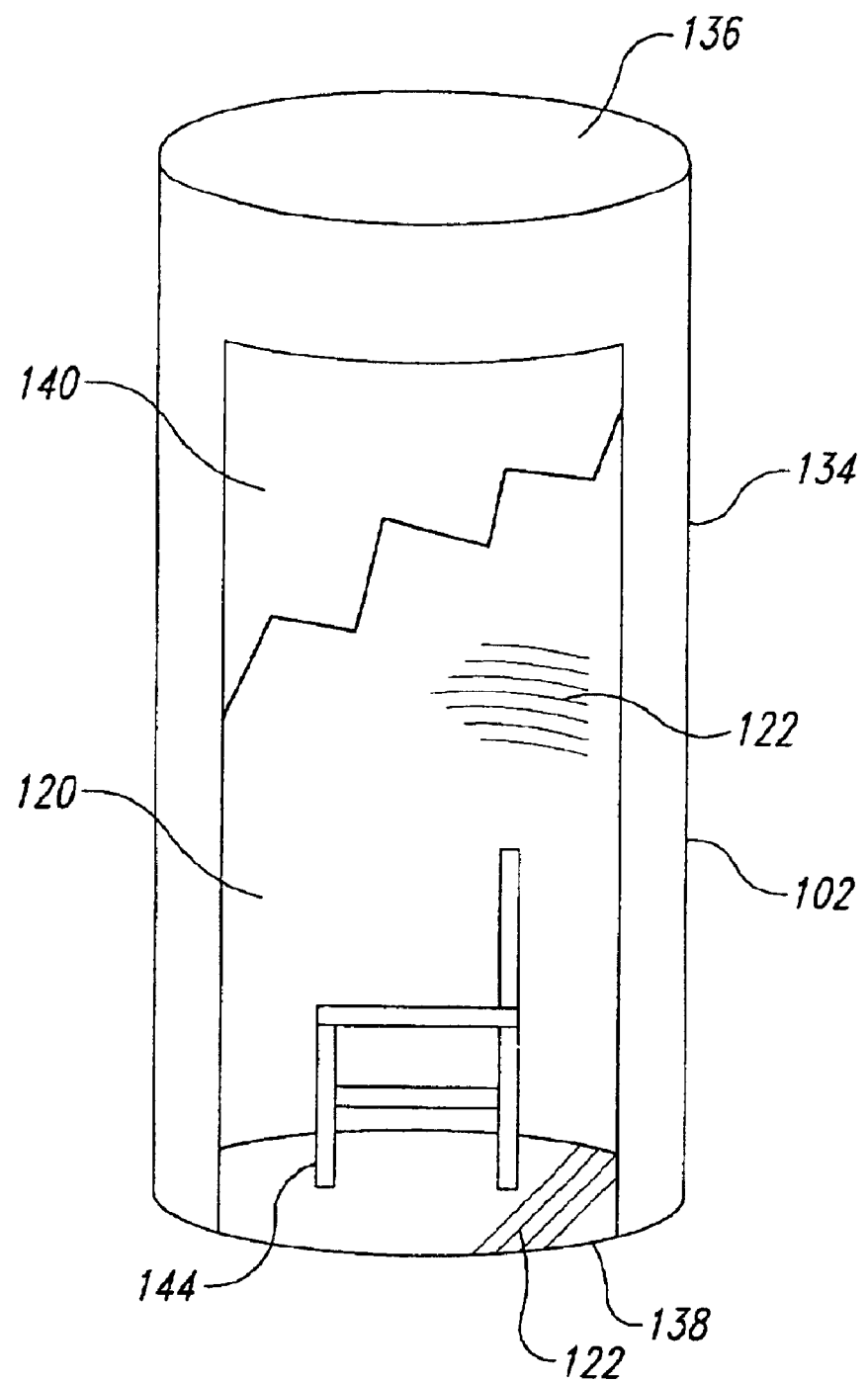
FIG. 4 is a partial cutaway perspective view of yet another alternative embodiment of the chamber of the present invention.

The chamber 102 illustrated in FIG. 3 is also formed with a hexagonal cross-section. However, the system 100 may be implemented with other shapes such as a triangular, rectangular, octagonal, or the like. The system 100 is not limited by the specific shape of the chamber 102. For example, FIG. 4 illustrates an embodiment of the chamber 102 with a circular sidewall 134 to form a cylindrical chamber. A circular top panel 136 and circular bottom panel 138 form part of the cylindrical chamber 102 in FIG. 4. The subject 104 (see FIGS. 1–3) enters and exits the interior portion 120 of the cylindrical chamber 102 via a door 140, which forms part of the circular sidewalls 134. The door 140 is illustrated in FIG. 4 in a partial cutaway view to allow viewing of the interior portion 120 of the cylindrical chamber 102. As with other embodiments, the reflective surface 122 is mounted to the interior side of the cylindrical sidewalls as well as the top 136 and bottom 138 of the chamber 102 to reflect energy emitted from the subject 104 (see FIGS. 1–3).

The cylindrical chamber 102 illustrated in FIG. 4 is also positioned in a substantially vertical orientation. However, other orientations may be used satisfactorily with the system 100. If the cylindrical chamber 102 is positioned in a substantially horizontal orientation, the support member 126 (see FIG. 2) may be used to permit placement of the subject 104 in the prone or supine position. In the vertical orientation illustrated in FIG. 4, the subject may stand within the interior portion 120 of the chamber 102 or may be positioned in a chair 144. Thus, the chamber 102 may be provided in a wide variety of cross-sectional shapes and sizes and may be positioned in various orientations. Although vertical and horizontal orientations have been illustrated herein, those skilled in the art can appreciate that other orientations for the chamber 102 may be readily provided.

The reflective surface 122 covers at least a portion of the interior surfaces of the chamber 102. In an exemplary embodiment, the reflective surfaces 122 substantially cover all the interior surfaces of the chamber 102. The dimensions of the chamber 102 are not critical and may be sized to accommodate a broad range of physical sizes of the subject 104.

Figure 5A:
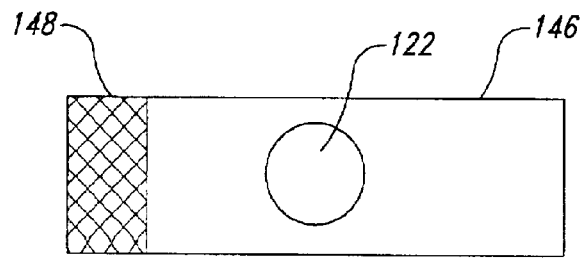
FIGS. 5a–5c are top plan views of alternative embodiments of reflective members of the present invention.
Figure 5B:
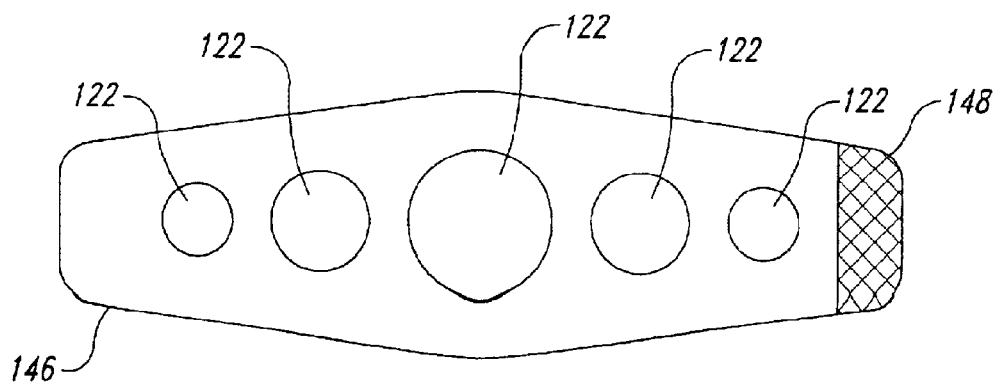
Figure 5C:
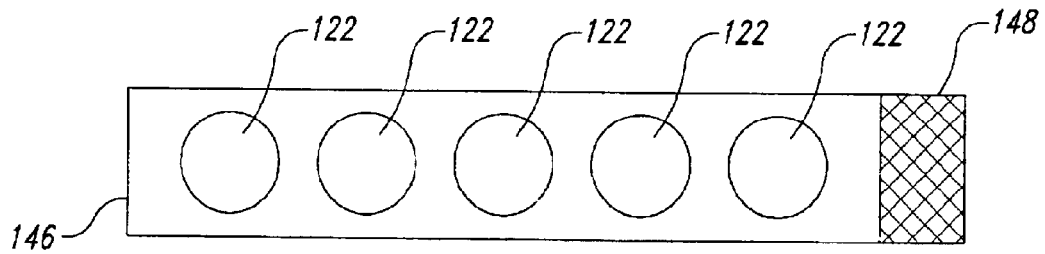

The photonic energy emitted from the subject 104 is reflected back to the subject to permit self-healing processes to occur. The self-healing process may be activated by directing monochromatic and/or coherent light onto the subject. In the embodiments illustrated in FIGS. 1–4, the subject is placed within the chamber 102 where reflective surfaces 120 covering some or all of the interior of the chamber reflect energy back to the subject 104. In this embodiment, energy generally emitted from the subject is reflected back thereto by virtue of the reflective surfaces 122. Such an embodiment promotes overall healing. For activation of healing directed to more specific portions of the subject 104, reflective surfaces may be positioned directly in contact with or in close proximity to the subject. FIGS. 5A–5C illustrate some of the many configurations of this alternative embodiment. For example, the reflective surface 122 may be mounted in a wrap 146. The reflective surface 122 is placed on the subject 104 at a location of injury, such as, by way of example, a wrist. The wrap 146 is wrapped around the subject 104 and may be held in place by a fastening member 148, such as Velcro™ or other suitable fastening material. Alternatively, the fastening member 148 may simply be tape to hold the reflective material 122 in the desired predetermined location on the subject 104.

The wrap 146 may be manufactured from any convenient material, such as cloth (e.g., cotton), elastic, neoprene, or the like. The present invention is not limited by the specific material used to construct the wrap 146 nor the fastening member 148.

Multiple reflective surfaces may also be used to activate healing processes over a larger surface area on the subject 104. This is illustrated in FIGS. 5B–5C where a plurality of reflective surfaces 122 are mounted within the wrap 146. In the embodiment illustrated in FIG. 5B, the reflective surfaces 122 vary in size. Alternatively, the multiple reflective surfaces 122 may be of substantially uniform size, such as illustrated in FIG. 5C. Although the reflective surfaces 122 are illustrated in FIGS. 5A–5C in circular form, other shapes may be readily used with the system 100. The present invention is not limited by the specific form of the reflective surfaces 122.

Figure 6:
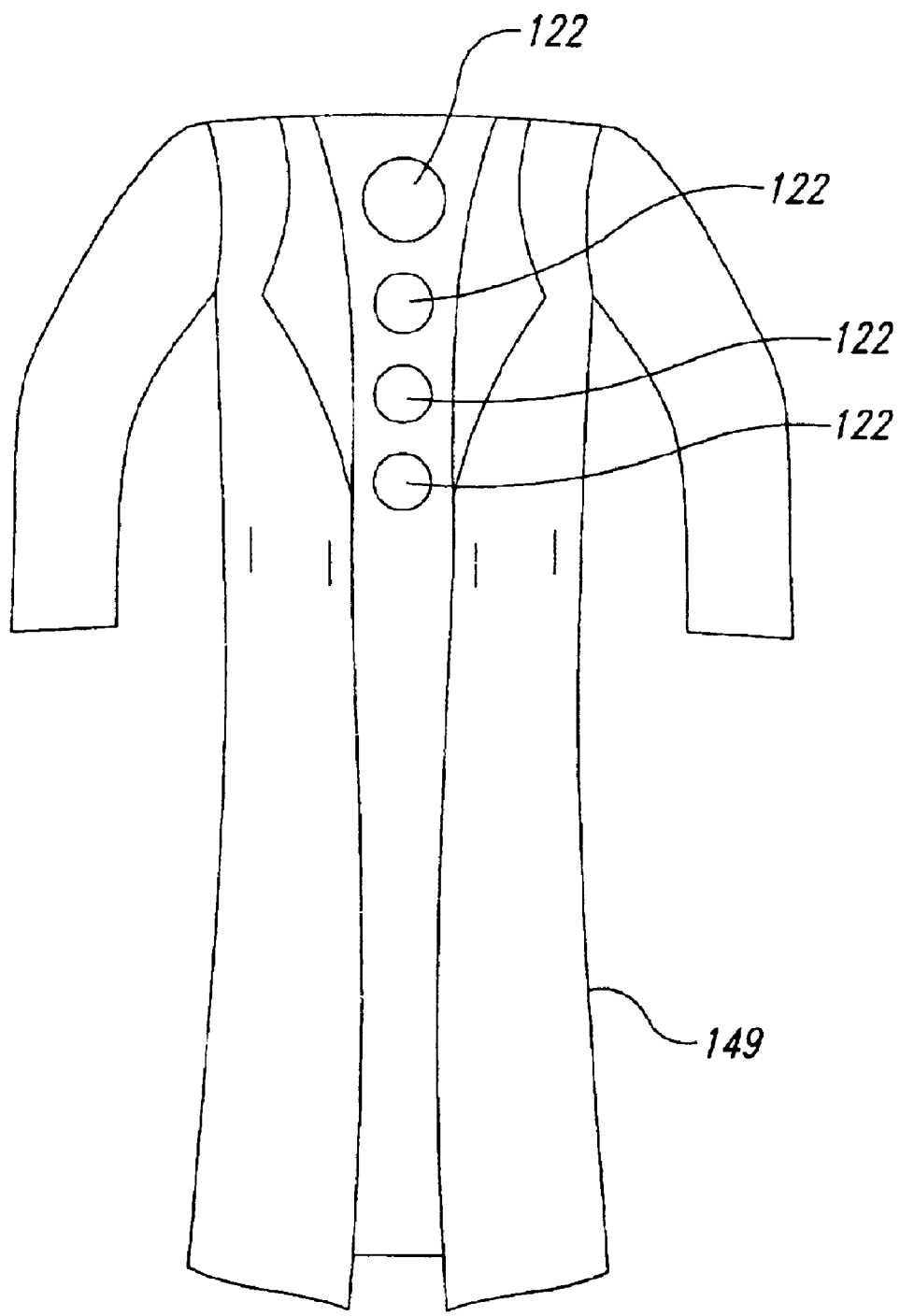
FIG. 6 is a front view of a garment containing reflective members in yet another alternative embodiment of the present invention.

In yet another alternative embodiment, the reflective surfaces 122 may be affixed inside a garment 149, as illustrated in FIG. 6. The garment 149 is designed to be worn by the subject 104. In the example illustrated in FIG. 6, the reflective surfaces 122 are positioned to come into proximity with the spine of the subject 104 when the garment 149 is worn by the subject. The reflective surfaces 122 may be permanently affixed to the garment 149, such as being sewed into position. Alternatively, the reflective surfaces 122 may be removably mounted to the garment 149 to permit cleaning of the garment and to permit positioning of the reflective surfaces at the desired location. For example, the reflective surfaces 122 may be moved to a position around the lower back of the subject 104. For the sake of brevity, this embodiment is not illustrated herein. However, those skilled in the art will recognize that the reflective surfaces 122 may be mounted in the garment 149 at convenient locations such that the reflective surfaces are proximate desired predetermined locations on the surface of the subject 104 when the garment is worn by the subject.

Figure 7:
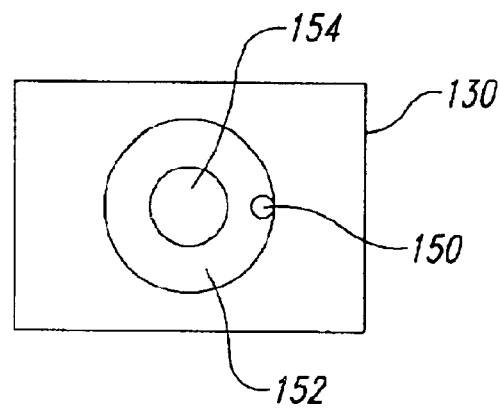
FIG. 7 is a top plan view of one embodiment of the light source of the present invention.
Figure 8:
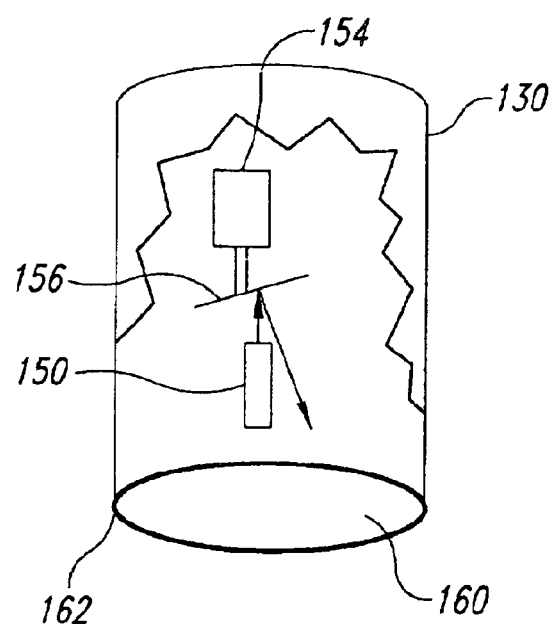
FIG. 8 is a partial cutaway perspective view of an alternative embodiment of the light source of the present invention.

As previously discussed, the light source 150 is mounted within a housing 130 illustrated in FIGS. 7 and 8. The particular shape of the housing is not critical to satisfactory operation of the system 100. FIG. 7 is a cutaway top plan view of a rectangular implementation of the housing 130, while FIG. 8 is a partial fragmentary perspective view of a circular housing 130. Returning again to FIG. 7, the light source 150 is mounted within the housing 130. An emission response of the body of the subject 104 is stimulated by directing the light source 150 onto the abdomen of the subject. In one embodiment, the subject may simply hold the light source 150 and direct it in a somewhat circular motion on a limited portion of the trunk of the subject 104. However, the implementations illustrated in FIGS. 7 and 8 provide an automated process for directing the light source 150 in a somewhat circular pattern onto the trunk of the subject 104. As illustrated in FIG. 7, the light source 150 is mounted on a peripheral edge of a rotating member 152, such as a disk. The rotating member is, in turn, coupled to a motor 154. The rotational velocity of the motor is not critical to satisfactory operation of the system 100. In an exemplary embodiment, the motor 154 rotates at approximately 200 revolutions per minute (RPM). The rotating member 152 is coupled to a shaft (not shown) of the motor and rotates therewith. The light source 150 thus rotates in a circular pattern in either a clockwise or counterclockwise direction, depending on the motor. Power may be supplied to the motor and to the light source 150 using a variety of known techniques. In an exemplary embodiment, the motor 154 is a DC motor that may be battery operated. This avoids the requirement for high-voltage AC power and minimizes shock risk to the subject 104 (see FIGS. 1–3). Power may be supplied to the light source 150 using conventional techniques, such as slip rings. In an exemplary embodiment, the light source 150 is also battery powered to reduce shock hazard to the subject 104.

In an exemplary embodiment, the light source 150 is a monochromatic light source, such as may be provided by filtered light or a device, such as a light-emitting diode designed to emit light of over a narrow band such that it may be considered monochromatic. In a further exemplary embodiment, the light source 150 may be a coherent light source. In one embodiment, the coherent light is provided by a laser, such as a class IIIA laser having a wavelength of approximately 670 nanometers (nm) and an output power of approximately 5.0 milliwatts (mW). It should be noted that the wavelength discussed above is in the visible region of the spectrum. However, other wavelengths of light may be satisfactorily used to implement the light source 150 in the system 100. Wavelengths within the visible and infrared region of the spectrum may be used satisfactorily with the system 100. In addition, other sources of coherent light may be used instead of a laser. The class III laser described above is selected for its convenient small size, low cost, and ease of operation with a battery.

In an alternative implementation shown in FIG. 8, the light source 150 may be fixed in position within the housing 130. The light source 150 is directed upward toward a mirror 156, which is mounted at an offset angle to the shaft of the motor 154. As the motor 154 rotates, the mirror 156 disperses the light and reflects it to the bottom portion of the housing 130. This implementation eliminates the need for a commutator or brush rings to supply power to the light source 150.

In an exemplary embodiment, the housing 130 is manufactured from a material that is opaque to the wavelengths of light emitted from the light source 150. For example, the housing may be readily manufactured from plastic or metal. The interior portion of the housing 130 may be coated with a dark color to absorb stray light emitted from the light source 150. The light exits the housing 130 through a bottom portion 160 of the housing 130. In an exemplary embodiment, the bottom portion 160 comprises clear glass such that the light source 150, motor 154, and other components are sealed within the housing 130. In an alternative embodiment, the bottom portion 160 may be manufactured from colored filter glass that is designed to pass only the wavelengths from the light source 150. For example, if the light source 150 is implemented with a class III laser having a wavelength of approximately 670 nm, the bottom portion 160 may be manufactured from glass or plastic, or other suitable material, that is designed to pass this wavelength. Such a filter arrangement prevents the passage of undesirable wavelengths and/or non-monochromatic light.

In yet another exemplary embodiment, the bottom portion 160 may be manufactured from glass, plastic, or other suitable material in the form of a lens to focus the light energy onto a selected portion of the trunk of the subject 104 (see FIGS. 1–3). The use of lenses to focus light is well-known in the art and need not be described in any greater detail herein.

The bottom portion 160 of the housing 130 is surrounded by an opaque member 162, which serves to define a limited area of the subject 104 to which light from the light source 150 will be applied. The opaque member 162 may be satisfactorily implemented using a variety of techniques. In one embodiment, the opaque member 162 may be a black circular O-ring, which may be manufactured from rubber or other suitable pliable material. The specific type of material used to implement the opaque member is not critical to satisfactory operation of the invention. An O-ring may be selected for its low cost and pliable nature to allow a complete seal when the housing 130 is pressed against the trunk of the subject 104. However, the opaque member 162 may be manufactured from other material, such as foam, plastic, or the like. The shape of the opaque member 162 is selected to correspond to the shape of the bottom portion 160 of the housing 130. If the housing 130 is made in a different shape, such as the rectangular housing of FIG. 5, the opaque member 162 may be designed to have a rectangular shape to match a rectangular bottom portion (not shown).

Figure 9:
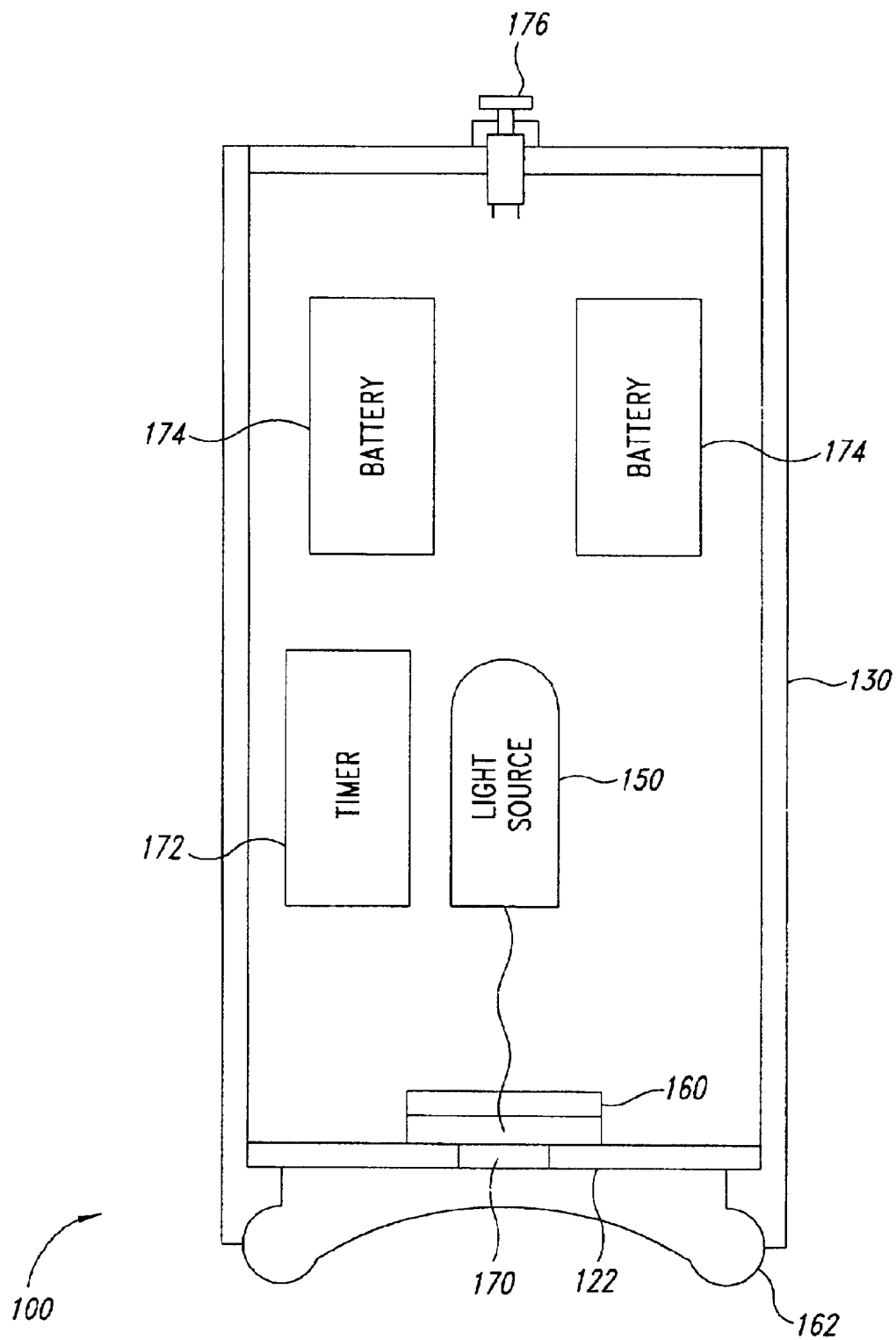
FIG. 9 is a cutaway side view of yet another alternative embodiment of the light source of the present invention.

FIG. 9 illustrates another exemplary embodiment of the housing 130 and light source 150 of the present invention. The light source 150 is mounted within the housing 130 and directs light onto the subject through the bottom portion 160 of the housing. In the embodiment illustrated in the cutaway side view of FIG. 9, the reflective surface 122 is also affixed to the housing 130. The reflective surface 122 is directed toward the subject 104 (see FIGS. 1–3) and reflects emissions radiated therefrom. Light from the light source 150 is directed through an aperture 170 in the reflective surface 122. Thus, light from the light source 150 is directed through the bottom portion 160, the aperture 170 and the reflective surface 122 and onto the subject 104.

The advantage of the self-contained unit illustrated in FIG. 9 is that the chamber 102 is not required. Thus, the system illustrated in FIG. 9 has the added advantage of easy portability. In addition, preliminary tests have indicated an increased efficacy for the localized treatment of dysfunction (e.g., injury, soreness, muscle spasms, inflammation, and the like) as compared to the chamber 102, which provides a more general reflection of light emissions from the subject 104. This is believed to result from increased amount of energy reflected back to the body at the point of dysfunction. The embodiment of FIG. 9 may also result in increased activation of the body's self-healing mechanisms by reflecting additional light from the light source 150 onto the subject 104. A portion of the light incident on the subject will be reflected. This reflected light strikes the reflective surface 122 and is reflected back onto the subject thus increasing the degree of activation of the self-healing mechanisms.

Also illustrated in FIG. 9 is a timer 172 and batteries 174. As discussed above, the system 100 is activated by pressing a switch 176, which triggers the timer 172. For the sake of clarity, internal wiring is not illustrated in FIG. 9. The timer 172 activates the light source 150 for a predetermined period of time (e.g., one minute). As noted above, the timer 172 is optional in the system 100. If the timer 172 is not included, the system 100 is activated so long as the switch 176 is active.

In yet another alternative embodiment, the light source 150 may be held in a fixed position with respect to the subject 104. That is, the light source 150 may be steadily directed to a specific location on the surface of the subject 104. In yet another alternative embodiment, the light source 150 may be pulsed or otherwise varied in intensity, In one embodiment, the light source 150 may be pulsed on and off at a frequency of approximately 60 Hz. In yet another alternative embodiment, the intensity of the light source 150 may be varied or modulated at a selected frequency.

The application of monochromatic and/or coherent light to a limited portion of the body of the subject 104 activates the emission of photons from the subject. The emitted photons are reflected back to the surface of the subject 104 to activate the process of self-healing. In a typical therapeutic treatment of the subject 104, the subject is placed in the interior portion 120 of the chamber 102. The subject may wear all natural fabric clothing, such as a cotton gown. Alternatively, the subject 104 may wear the garment 149 (see FIG. 6) containing one or more reflective surfaces 122 or may be fitted with the wrap 146 (see FIGS. 5a–5c) containing one or more of the reflective surfaces. The housing 130 containing the light source 150 is placed against the trunk of the subject 104. In the horizontal orientation illustrated in FIG. 2, the housing 130 is place on the body of the subject 104. In an alternative embodiment, the housing 130 may be attached to the support member 126 such that the housing makes contact with the body of the subject 104 when the subject reclines on the support member. If the chamber 102 is configured in a vertical orientation, such as illustrated in FIG. 3, or if the subject 104 is wearing the reflective surfaces, as illustrated in FIGS. 5a–5c and FIG. 6, the subject may hold the housing 130 against their trunk. Alternatively, a conventional mounting bracket (not shown) may be used to support the housing 130. In this embodiment, the subject 104 simply moves into position such that the body of the subject is placed against the housing 130. In an exemplary embodiment, the subject 104 may be placed in the chamber 102 and positioned approximately six inches from the reflective surface 122. The light source 150 is activated for a therapeutic period of time. In an exemplary embodiment, the light source 150 is activated for approximately one minute while the light moves in a somewhat circular pattern. In an exemplary embodiment, the monochromatic and/or coherent light from the light source 150 is moved in a clockwise direction in a somewhat circular pattern to direct the coherent light against the trunk of the subject 104. In an alternative embodiment, the light source 150 may be held in a substantially fixed location with respect to the subject 104. The light source 150 may have a fixed intensity or a varying intensity, as described above. As those skilled in the art can appreciate, various combinations of the light source 150 may also be provided in the system 100. For example, the light source 150 may be aimed at a fixed location with respect to the subject and varied in intensity or may have a fixed intensity. In yet another embodiment, the light source 150 may be moved manually or automatically with respect to the subject 104 and may also have either a fixed intensity or a varying intensity. Thus, the present invention is not limited by the specific implementation of the light source 150.

The light source 150 may be automatically activated by the switch 176 of FIG. 9 mounted to the housing such that the light source is activated when the housing 130 is pressed against the body of the subject 104. Alternatively, the light source 150 may be activated by a handheld switch (not shown) or from a switch outside the chamber 102. The duration of activation of the light source 150 may be automatically controlled using, by way of example, a timer 172 (see FIG. 9). The operation of the timer 172 is well known in the art and need not be described in greater detail herein.

A single application of monochromatic and/or coherent light from the light source 150 may be sufficient to activate the self-healing processes. In an alternative embodiment, a second application of light from the light source 150 may be applied. Following the application of light from the light source 150 to the body of the subject 104 for therapeutic period of time (e.g., approximately one minute) the subject may turn to apply the light from the light source to the other side of the subject. For example, if the subject 104 has been in the supine position, as illustrated in FIGS. 1 and 2, the subject may move into the prone position such that the light from the light source 150 is now applied to the other side of the subject. If the chamber 102 is configured in a substantially vertical orientation, the subject 104 may simply turn around so that the light from the light source 150 is applied to the other side of the subject. The light source 150 may be activated a second time for a therapeutic period of time. In an exemplary embodiment, the light source 150 may be activated for approximately one minute.

In an exemplary embodiment, the housing 130 of FIG. 9 is placed against the subject at the point of dysfunction and the light source 150 activated for a therapeutic period of time. The light source 150 may be automatically controlled by the timer 172 or manually controlled. As described above, the light source 150 may generate a fixed power or intensity light or can generate a variable power or intensity light. The housing 130 may be held in a fixed position relative to the point of dysfunction or moved about to the area of dysfunction.

In the exemplary embodiment discussed above, the light from the light source 150 is applied for a therapeutic time of approximately one minute to one or both sides of the subject 104. However, the length of exposure of the subject to light from the light source 150 may be increased. In the embodiment discussed above wherein the light source 150 is a laser having an output power of approximately 5.0 mW, there is no danger to the subject 104 from longer periods of exposure. It is important to recognize that light from the light source 150 should never be directed into the eyes of the subject 104 or any other person as it may damage the eyes. However, application of the light from the light source 150 to the body of the subject 104 for a therapeutic period of time poses little or no risk. The application of the light from the light source 150 advantageously activates the light emission/healing response cycle described above.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A system for the delivery of light energy to a subject, comprising:
   a container;
   a monochromatic light source within the container to deliver monochromatic light to the subject;
   a visually transparent bottom portion of the container to permit the passage of the light therethrough; and
   a reflective surface affixed to the exterior of the container proximate the bottom portion and directed toward a surface of a subject to reflect electromagnetic energy from the subject surface wherein the reflective surface is a mirrored surface.

2. A system for the delivery of light energy to a subject, comprising:
   a container
   a monochromatic light source within the container to deliver monochromatic light to the subject;
   a visually transparent bottom portion of the container to permit the passage of the light therethrough; and
   a reflective surface affixed to the container proximate the bottom portion and directed toward a surface of a subject to reflect electromagnetic energy from the subject surface and further comprising a motor within the container, the light source being coupled to the motor and moving therewith to thereby direct the light to a variable area on the surface of the subject.

3. A system for the delivery of light energy to a subject, comprising:
   a container;
   a monochromatic light source within the container to deliver monochromatic light to the subject;
   a visually transparent bottom portion of the container to permit the passage of the light therethrough; and
   a reflective surface affixed to the exterior of the container proximate the bottom portion and directed toward a surface of a subject to reflect electromagnetic energy from the subject surface wherein the visually transparent bottom portion comprises a clear glass surface.

4. A system for the delivery of light energy to a subject, comprising:
   a container;
   a monochromatic light source within the container to deliver monochromatic light to the subject;
   a visually transparent bottom portion of the container to permit the passage of the light therethrough; and
   a reflective surface affixed to the container proximate the bottom portion and directed toward a surface of a subject to reflect electromagnetic energy from the subject surface wherein the visually transparent bottom portion comprises a glass surface shaped to form a lens to thereby focus the light in a predetermined manner.

5. A system for the delivery of light energy to a subject, comprising:
   a container
   a monochromatic light source within the container to deliver monochromatic light to the subject;
   a visually transparent bottom portion of the container to permit the passage of the light therethrough; and
   a reflective surface affixed to the container proximate the bottom portion and directed toward a surface of a subject to reflect electromagnetic energy from the subject surface wherein the visually transparent bottom portion comprises a filter to permit passage of selected wavelengths of light generated by the light source.

6. A system for the delivery of light energy to a subject, comprising:
   a container;
   a monochromatic light source within the container to deliver monochromatic light to the subject;
   a visually transparent bottom portion of the container to permit the passage of the light therethrough; and
   a reflective surface affixed to the container proximate the bottom portion and directed toward a surface of a subject to reflect electromagnetic energy from the subject surface wherein the reflective surface comprises a centrally located non-reflective surface to permit passage of light from the light source.

7. A system for the delivery of light energy to a subject, comprising:
   a container;
   a monochromatic light source within the container to deliver monochromatic light to the subject;

a visually transparent bottom portion of the container to permit the passage of the light therethrough; and a reflective surface affixed to the container proximate the bottom portion and directed toward a surface of a subject to reflect electromagnetic energy from the subject surface wherein the reflective surface comprises a centrally located aperture to permit passage of light from the light source.

8. A system for the delivery of light energy to a subject, comprising:

a container;

a monochromatic light source within the container to deliver monochromatic light to the subject;

a visually transparent bottom portion of the container to permit the passage of the light therethrough; and a reflective surface affixed to the container proximate the bottom portion and directed toward a surface of a subject to reflect electromagnetic energy from the subject surface, further comprising an opaque sealing member surrounding the visually transparent bottom portion to prevent the application of light outside the opaque member when the bottom portion of the container is placed in contact with the subject.

9. A method for the delivery of light energy to a subject, comprising:

positioning a container containing a light source in proximity with the subject, having top and side portions that do not permit the passage of light therethrough and a visually transparent bottom portion to permit the passage of the light therethrough;

positioning a reflective surface outside of the container in proximity with the surface of a subject to reflect energy; and directing the light from the light source through the transparent bottom portion and onto the subject for a therapeutic period of time wherein the reflective surface is a mirrored surface.

10. A method for the delivery of light energy to a subject, comprising:

positioning a container containing a light source in proximity with the subject, having top and side portions that do not permit the passage of light therethrough and a visually transparent bottom portion to permit the passage of the light therethrough;

positioning a reflective surface outside of the container in proximity with the surface of a subject to reflect energy; and directing the light from the light source through the transparent bottom portion and onto the subject for a therapeutic period of time wherein directing the light comprises moving the light with respect to the subject to thereby direct the light to an area on the surface of the subject.

11. A method for the delivery of light energy to a subject, comprising:

positioning a container containing a light source in proximity with the subject, having top and side portions that do not permit the passage of light therethrough and a visually transparent bottom portion to permit the passage of the light therethrough;

positioning a reflective surface in proximity with the surface of a subject to reflect energy; and directing the light from the light source through the transparent bottom portion and onto the subject for a therapeutic period of time wherein the visually transparent bottom portion comprises a clear glass surface.

12. A method for the delivery of light energy to a subject, comprising:

positioning a container containing a light source in proximity with the subject, having top and side portions that do not permit the passage of light therethrough and a visually transparent bottom portion to permit the passage of the light therethrough;

positioning a reflective surface in proximity with the surface of a subject to reflect energy; and directing the light from the light source through the transparent bottom portion and onto the subject for a therapeutic period of time wherein the visually transparent bottom portion comprises a glass surface shaped to form a lens to thereby focus the light in a predetermined manner.

13. A method for the delivery of light energy to a subject, comprising:

positioning a container containing a light source in proximity with the subject, having top and side portions that do not permit the passage of light therethrough and a visually transparent bottom portion to permit the passage of the light therethrough;

positioning a reflective surface in proximity with the surface of a subject to reflect energy; and directing the light from the light source through the transparent bottom portion and onto the subject for a therapeutic period of time wherein the visually transparent bottom portion comprises a filter to permit passage of selected wavelengths of light generated by the light source.

14. A method for the delivery of light energy to a subject, comprising:

positioning a container containing a light source in proximity with the subject, having top and side portions that do not permit the passage of light therethrough and a visually transparent bottom portion to permit the passage of the light therethrough;

positioning a reflective surface in proximity with the surface of a subject to reflect energy; and directing the light from the light source through the transparent bottom portion and onto the subject for a therapeutic period of time and further comprising mounting an opaque sealing member surrounding the visually transparent bottom portion to prevent the application of light outside the opaque member when the bottom portion of the container is positioned proximate to the subject.

* * * * *

UNITED STATES PATENT AND TRADEMARK OFFICE
CERTIFICATE OF CORRECTION

| | | |
|---|---|---|
| PATENT NO. | : 6,811,565 B2 | Page 1 of 1 |
| APPLICATION NO. | : 09/991129 | |
| DATED | : November 2, 2004 | |
| INVENTOR(S) | : Denton et al. | |

It is certified that error appears in the above-identified patent and that said Letters Patent is hereby corrected as shown below:

In Column 2, Line 11, change "3", to --III--.

In Column 2, Line 22, after "alternative" insert -- embodiment--.

In Column 3, Line 14, after "inflammation" insert --,--.

In Column 4, Line 12, delete "a".

In Column 4, Line 57, change "120" to --122--.

In Column 6, Line 17, delete "of".

In Column 7, Line 65, change "," to --.--.

In Column 8, Line 17, change "place" to --placed--.

In Column 9, Line 3, before "therapeutic", insert --a --.

In Column 9, Line 19, after "150", insert --is --.

In Column 9, Line 65, after "container", insert --;--.

In Column 10, Line 38, after "container", insert --;--.

Signed and Sealed this

Twentieth Day of November, 2007

JON W. DUDAS
*Director of the United States Patent and Trademark Office*